(12) United States Patent
Carlson (10) Patent No.: US 6,906,239 B2
(45) Date of Patent: Jun. 14, 2005

(54) PLANT PREPARATIONS (76) Inventor: Peter S. Carlson, 3600 Inverness Dr., Chevy Chase, MD (US) 20815

( * ) Notice: Subject to any disclaimer, the term of this patent is extended or adjusted under 35 U.S.C. 154(b) by 26 days.

(21) Appl. No.: 10/366,720

(22) Filed: Feb. 14, 2003

(65) Prior Publication Data

US 2003/0226168 A1 Dec. 4, 2003

Related U.S. Application Data (60) Provisional application No. 60/403,650, filed on Aug. 16, 2002, and provisional application No. 60/356,730, filed on Feb. 15, 2002.

(51) Int. Cl.$^7$ .......................... A01H 1/00; C12N 15/82; C12N 15/87; C12Q 1/18
(52) U.S. Cl. ......................................... 800/279; 435/32
(58) Field of Search ............................ 800/279; 435/32

(56) References Cited

PUBLICATIONS

Li et al.;5–Hydroxyconiferyl Aldehyde Modulates Enzymatic Methylation for Syringyl Monolignol Formation, a New View of Monolignal Biosynthesis in Angiosperms; the Journal of Biological Chemistry; vol. 275, No. 9; 6537–6545; Mar. 3, 2000.*

Perry, "Natural Products from New Zealand Plants," Chapter 5 in ACS Symposium Series 774, Agrochemical Discovery, Baker et al., eds. (2001), pp. 48–61.

Strack, "Phenolic Metabolism," Chapter 10 in Plant Biochemistry, Dey et al., eds. Academic Press (1997), pp. 387–410.

Douglas, "Phenylpropanoid Metabolism and Lignin Biosynthesis: from Weeds to Trees," Trends in Platn Science, (1996), vol. 1, No. 6, pp. 171–178.

Ishii, "Structure and Functions of Feruloylated Polysaccharides," Plant Science (1997), vol. 127, pp. 111–127.

Carbon Sequestration Research and Development, Report, U.S. Department of Energy, Chapter 4, pp. 4–1 to 4–29 (Dec. 1999).

Myneni, "Formation of Stable Chlorinated Hydrocarbons in Weathering Plant Material," *Science*, vol. 295, pp. 1039–1041 (Feb. 2002).

Whetten et al., "Lignin Biosynthesis," *The Plant Cell*, vol. 7, 1001–1013 (Jul. 1995).

M.A. Phillips, et al., "Resin–based Defenses in Conifers", *Trends in Plant Science*, May 1999, vol. 4, No. 5, pp. 184–190.

* cited by examiner

*Primary Examiner*—Kent Bell
(74) *Attorney, Agent, or Firm*—Foley & Lardner, LLP (57) ABSTRACT The present invention provides methods for slowing down the rate at which plant biomaterials, such as lignin, are degraded, thereby improving the terrestrial storage of carbon by reducing the amount of gaseous carbon dioxide released into the atmosphere upon biodegradation. The inventive methods contemplate the modification of plant macromolecules to make them more resistant to degradation as well as the treatment of living and non-living plants with fungicides to prolong the rate of plant breakdown.

13 Claims, 4 Drawing Sheets

PLANT PREPARATIONS

FIELD OF THE INVENTION

The present invention provides methods and materials to improve terrestrial storage of carbon in decaying plant biomass by incorporating modified macromolecule precursors into key plant structures, thereby improving the ability of plant biomass to withstand environmental degradation and the activity of degradative microorganisms. Modified lignin or modified lignin precursors incorporated into plant biomass reduces the rate of degradation of lignin in soil. Furthermore, the antimicrobial activity of lignin breakdown products protects plants from degradative microorganisms. This technology reduces the rate at which carbon dioxide is released into the atmosphere when plant and soil organic matter are treated with the inventive molecules. Thus, the present invention increases the amount of carbon that is sequestered in a terrestrial ecosystem.

BACKGROUND

An aspect of carbon sequestration is the prevention of carbon dioxide emission into the atmosphere and the improved retention of carbon in terrestrial ecosystems. Combustion of fossil fuel, such as for power generation, transport, industry and domestic use, is a major factor in increasing the concentration of carbon dioxide in the atmosphere. Consequently, elevated levels of carbon dioxide can be detrimental to the environment, causing, for instance, global warming and fluctuations in global climates. For this reason, stabilizing and reducing the concentration of gaseous carbon, such as $CO_2$, is a necessary step in diminishing the effects of warming trends, while simultaneously extending the time period within which technologies for mitigating $CO_2$ emissions can be further developed.

One way to uncouple fossil fuel usage and $CO_2$ levels is to improve the storage of carbon within terrestrial biomass. In this respect, plants and other worldwide vegetation are natural $CO_2$ "sinks" that continually remove and trap gaseous carbon from the atmosphere by processes such as photosynthesis. On a global scale, plants represent an enormous quantity of stored carbon. Taken collectively, the terrestrial biosphere is estimated to sequester approximately 2 gigatonnes of carbon (GtC) per year. Of that biomass, the most abundant component of terrestrial plant materials are cellulose and lignin, which represent key carbon stores. Lignin is a very complex, aromatic macromolecule, used to form plant cell walls and structural tissues. The molecule imparts strength to the plant, facilitates water transport and impedes biodegradation of plant polysaccharides and protects plants against microbial attack. Plants that have a high lignin content, may, therefore, store a substantial amount of carbon while simultaneously being very difficult to degrade.

Nevertheless, when plant litter becomes incorporated into soil and components such as lignin are eventually broken down, the once-trapped carbon can be liberated by any number of degradative factors, especially by microbes and biochemical processes, such as oxidation. In fact, oxidation of terrestrial soil carbon is estimated to release approximately 0.5 billion tonnes into the atmosphere. Cultivation, for instance, exposes fresh soil to the air, increasing the rate of carbon dioxide emission.

Furthermore, fungi such as white-rot fungi and wood-rotting fungi, as well as a variety of bacterial and actinomycetes species, appear to be the most efficient lignin-degraders present in terrestrial ecosystems. For instance, white-rot fungi produce "lignase" peroxidase enzymes that produce free oxygen radicals that are potent lignin decomposers. Thus, a major cause of $CO_2$ release from soil organic materials is the increased accessibility of carbon to elements that are capable of converting one form of carbon into another.

Accordingly, the rate at which carbon dioxide is produced depends upon both the surrounding environmental conditions and upon the ease by which plant materials can be broken down. Thus, the decomposability of soil organic matter reflects the nature of its chemical components. In this regard, some plant detritus and microbial biomass have a relatively short turnover time, generally less than 10 years. In contrast, soil organic carbon is more resistant to microbial degradation and takes between 10 and 100 years to break down. Since approximately 75% of terrestrial carbon is stored within soil organic material, the adaptation of soil to better retain that carbon is one focus of recent sequestration efforts.

For these reasons, there have been efforts to modify terrestrial vegetation, soil and plant-derived organic matter, so that the sequestered carbon is more difficult to access, utilize and, thus liberate.

To this end, "no-till" practices have been adopted to reduce the exposure of "fresh" soil to oxidative processes. Another is the transportation of natural organic matter to deep groundwater systems where the residence time of such materials is hundreds, if not thousands, of years. However, this latter method relies upon heavy rainfall or other similarly intense precipitation after prolonged dry periods, to wash organically-stored carbon into underground sites. Planting new trees and forest fertilization are other methods by which the terrestrial biosphere is being adapted so as to improve carbon sequestration.

There is still a need, however, for better methods of retaining carbon in soil, such as by actually modifying the terrestrial organic material that eventually becomes soil. For instance, a key query is whether the formation of "highly-recalcitrant organic macromolecules" can be enhanced through "solid amendments, microbial manipulation, or genetic selection of biomass." See Chapter 4 of CARBON SEQUESTRATION RESEARCH AND DEVELOPMENT, December 1999 Report, U.S. Department of Energy, available at http://www.fe.doe.gov/coal_power/sequestration/reports/rd/. With regard to the latter, efforts have focused on genetic manipulation of plants. Research is being conducted on modifying the genes of perennial plants to provide resistance to microbial degradation. See 4–19 of CARBON SEQUESTRATION RESEARCH AND DEVELOPMENT.

Another suggested approach along these lines, involves the reintroduction of genetic stocks of plants that possess higher lignin content into the biomass so as to improve carbon sequestration and to better inhibit the ability of microorganisms to decompose soil organic material. However, recombinant genetic approaches can require substantial research and development efforts and stringent control of the gene carriers that are used to introduce and incorporate foreign genes into plant genomes.

Thus, there is a need for methods that would alter the "composition of cellular components" and increase "energy content, durability and lignin content" in order to reduce decomposition rates and to improve microbial and disease resistance. See CARBON SEQUESTRATION RESEARCH AND DEVELOPMENT, a U.S. Department of Energy Report, Office of Science, December 1999.

A recent publication by Myneni (*Science*, 295, 1039–1041, 2002), showed that the halogen, chlorine, is naturally-occurring in plant organic materials. Indeed, Myneni showed that "organo-Cl" compounds are "the dominant forms of [chlorine] in the organic fraction of soils, sediments and aquatic systems in humified organics of all examined plant samples." See page 1040. He states that the naturally-occurring chlorinated derivatives of organic molecules are recalcitrant in nature to "biotic and abiotic transformations." See page 1041.

However, Myneni, describes only naturally occurring organo-chlorinated compounds that are created only after the death and degradation of a plant and its composite biomolecules. Moreover, the chlorine is added to organic molecules by the activity of fungal and microbial enzymes after death and degradation of the plant. Furthermore, the concentration of chlorinated organic compounds in humified plant material is less than 10 mM $Kg^{-1}$. The plant-derived, "organo-Cl" compound is, therefore, a normal constituent of the environment, but is nevertheless, an uncontrollable entity in the environment.

The present invention solves these problems by providing a novel and efficient method for altering the composition of cellular materials, particularly lignin content, so as to reduce the rate at which the biodegradation of soil organic materials, such as lignin, occurs, while also enhancing the antimicrobial properties of lignin degradation products.

SUMMARY

Thus, by incorporating modified chemical precursors into plant macromolecules, the present invention reduces the rate at which plant biomass decays and in so doing, improves the terrestrial storage of carbon over time. Hence, the present invention enhances the ability of the plant biomass to withstand environmental degradation and microbial attack. Furthermore, a modified chemical precursor that is contained within a plant breakdown product, such as a lignin degradation product, can help to enhance the antimicrobial properties of those degradation products. What is more, the present invention provides methods and assays for determining which modified precursors may be most beneficial in terms of enhancing the antimicrobial properties of a lignin degradation product.

In one embodiment, any lignin-containing plant may be treated with a modified precursor according to the instant invention. In a preferred embodiment, the plant is a plant that is capable of taking up a preparation of a molecule that comprises a chemical group that is not a natural consituent of a macromolecule of the plant, such as a modified lignin precursor. In another embodiment, the preparation of a modified precursor may be a liquid, a powder, a gel, or a gas. In a preferred embodiment the preparation of a modified precursor is a liquid that can be applied to the roots of the plant to be treated. In a further embodiment, the preparation may include other chemicals or compounds, such as a herbicide or a plant growth regulator. In a preferred embodiment, glyphosate and glyophosine may each be added to a preparation of a modified precursor, independently or together.

Another aspect of the present invention is a screening assay for determining the antimicrobial properties of a plant macromolecule that contains a molecule that comprises a chemical group that is not a natural consituent of a macromolecule of the plant.

In a preferred embodiment, the screening assay comprises treating a plant, or part thereof, with a molecule, such as a modified lignin precursor; culturing a degradative microorganism on the treated plant sample and on an untreated plant sample; and determining, after a period of incubation, how much of the microorganism is present in or on the treated plant samples in comparison to the untreated plant sample. Preferably, the molecule is a component of a natural biosynthetic pathway in the plant, and becomes incorporated into a resultant plant macromolecule. In another preferred embodiment, a decrease in the amount of the degradative microorganism with respect to an untreated plant sample is indicative of the antimicrobial properties of the plant macromolecule.

In a preferred embodiment, the step of treating the plant sample with a molecule that comprises a chemical group that is not a natural consituent of a macromolecule of the plant, is performed by at least one of a spray, an injection, an external application, or a drench.

In another preferred embodiment, the plant is any lignin-producing plant or any lignin-containing plant.

In another preferred embodiment, the molecule that is applied to the plant is a modified lignin precursor. In a more preferred embodiment, the modified lignin precursor is a modified monolignol selected from the group consisting of a para-coumaryl alcohol, a coniferyl alcohol or a sinapyl alcohol. In another preferred embodiment, the modified precursor is an acid or an aldehyde derivative of para-coumaryl alcohol, a coniferyl alcohol or a sinapyl alcohol.

In yet another embodiment, a sinapate, ferulate, cinnamate, sinapoyl aldehyde, coniferyl aldehyde, or cinnamyl aldehyde precursor may be modified according to the instant invention. In yet one other embodiment, the modified precursor may be a modified cinnamic acid molecule.

In a more preferred embodiment, the modified precursor may be any C6-C1, C6-C2 and C6-C3 molecule that contains an unnaturally-occurring chemical group or a naturally-occurring group at an unnatural position on the C6 aromatic ring. In one embodiment, the unnaturally-occurring chemical group may be a halogen, an amide, an amino, a nitro-group, a hydroxymethyl, a hydroxy, a sulfur and a methyl. In another embodiment, an "unnatural position" on the C6 aromatic ring may be any one of positions 1–6 that normally does not contain a naturally-occurring group.

In a more preferred embodiment, the modified precursor is a modified C6-C3 molecule. In another preferred embodiment, the modified C6-C3 molecule is a cinnamic acid-characterized molecule.

In a further aspect, the modified precursor is a mixture of at least any two of a para-coumaryl alcohol, a coniferyl alcohol or a sinapyl alcohol or their acid or aldehyde derivatives.

In yet another embodiment, the degradative microorganism is a white-rot fungus, a wood-rotting fungus, a bacteria species or an actinomycete species.

In a preferred embodiment, the step of determining how much degradative microorganism is present in or on the treated plant sample in the screening assay, comprises determining chitin content. In a preferred embodiment, the plant sample is stained for chitin. In the latter embodiment, an intense chitin stain in the treated plant sample indicates microbial growth, and wherein a less intense chitin stain in the treated plant sample indicates inhibition of microbial growth. In a preferred embodiment, the intensity of the chitin stain is compared to a untreated plant sample control. In another preferred embodiment, the untreated plant sample control is a plant sample that has not been treated with a modified precursor.

In yet another embodiment, the treated plant sample is stained for lignin. In a further embodiment, the intensity of the lignin stain is compared to the intensity of staining of an untreated control plant sample. In one embodiment, the relative amount of lignin present in the treated plant sample is determined by the intensity of the lignin stain.

In a further embodiment, the step of determining how much degradative microorganism is present in or on the treated plant sample, comprises performing an MIC screening assay. In this instance, a large zone of inhibition of microorganism growth around the treated plant sample indicates that the modified precursor has an effective antimicrobial property.

In another aspect of the instant invention, a lignin prodrug is provided that comprises at least one modified precursor. In a preferred embodiment, the prodrug is activated upon degradation of the lignin to produce lignin degradation products that have antimicrobial activity.

In a preferred embodiment, the lignin prodrug contains at least one of a C6-C1, C6-C2 or a C6-C3 modified precursor. In yet another embodiment, the modified precursor is a para-coumaryl, a coniferyl or a sinapyl, or any one of their acid or aldehyde derivatives.

In yet a further aspect, the present invention provides an activated lignin antimicrobial, comprising at least one modified lignin degradation product.

In a preferred embodiment, the activated lignin antimicrobial is a degradation product that comprises a C6-C1, a C6-C2 or a C6-C3 molecule that contains an unnaturally-occurring chemical group. In a preferred embodiment, the unnaturally-occurring chemical group is any one of a halogen, an amide, an amino, a nitro, a hydroxymethyl, a hydroxy, a sulfur or a methyl group. In another preferred embodiment, the modified lignin degradation product comprises at least one modified monolignol precursor selected from the group consisting of a modified para-coumaryl alcohol, a coniferyl alcohol or a sinapyl alcohol. In another embodiment, the modified precursor is an acid or aldehyde derivative of para-coumaryl alcohol, a coniferyl alcohol or a sinapyl alcohol.

The present invention further provides another screening assay for determining the antimicrobial properties of a modified precursor molecule. In this respect, one embodiment of the screening assay comprises treating a plant sample with a modified lignin precursor; producing a fibrous material from the treated plant sample; exposing the fibrous material to a highly oxidizing environment; adding a microorganism to the exposed fibrous material; and determining the extent of growth of the microorganism on the treated plant sample. A decrease in the growth of the degradative microorganism, with respect to an untreated control plant sample, is indicative of the antimicrobial properties of the modified precursor.

In one embodiment, the treating step is performed by at least one of a spray, injection, external application, or drench.

In another preferred embodiment, the plant is any lignin-producing plant or any lignin-containing plant.

In another preferred embodiment, the modified precursor is a modified lignin precursor. In a more preferred embodiment, the modified lignin precursor is a modified monolignol selected from the group consisting of a para-coumaryl alcohol, a coniferyl alcohol or a sinapyl alcohol. In another preferred embodiment, the modified precursor is an acid or an aldehyde derivative of para-coumaryl alcohol, a coniferyl alcohol or a sinapyl alcohol.

In yet another embodiment, a sinapate, ferulate, cinnamate, sinapoyl aldehyde, coniferyl aldehyde, or cinnamyl aldehyde precursor may be modified according to the instant invention. In yet one other embodiment, the modified precursor may be a modified cinnamic acid molecule.

In a more preferred embodiment, the modified precursor may be any C6-C1, C6-C2 and C6-C3 molecule that contains an unnaturally-occurring chemical group or a naturally-occurring group at an unnatural position on the C6 aromatic ring. In one embodiment, the unnaturally-occurring chemical group may be a halogen, an amide, an amino, a nitro-group, a hydroxymethyl, a hydroxy, a sulfur and a methyl. In another embodiment, an "unnatural position" on the C6 aromatic ring may be any one of positions 1–6 that normally does not contain a naturally-occurring group.

In a more preferred embodiment, the modified precursor is a modified C6-C3 molecule. In another preferred embodiment, the modified C6-C3 molecule is a cinnamic acid-characterized molecule.

In a further aspect, the modified precursor is a mixture of at least any two of a para-coumaryl alcohol, a coniferyl alcohol or a sinapyl alcohol or their acid or aldehyde derivatives.

In yet another embodiment, the degradative microorganism is a white-rot fungus, a wood-rotting fungus, a bacterial species or an actinomycete species.

In a preferred embodiment, the step of determining how much degradative microorganism is present in or on the treated plant sample in the screening assay comprises determining chitin content, wherein an intense chitin stain in the treated plant sample indicates microbial growth, and wherein a less intense chitin stain in the treated plant sample indicates inhibition of microbial growth. In a preferred embodiment, the intensity of the chitin stain is compared to a untreated plant sample control. In another preferred embodiment, the untreated plant sample control is a plant sample that has not been treated with a modified precursor.

In yet another embodiment, the treated plant sample is stained for lignin. In a further embodiment, the intensity of the lignin stain is compared to the intensity of staining of an untreated control plant sample. In one embodiment, the relative amount of lignin present in the treated plant sample is determined by the intensity of the lignin stain.

In a further embodiment, the step of determining how much degradative microorganism is present in or on the treated plant sample, comprises performing an MIC screening assay. In this instance, a large zone of inhibition of microorganism growth around the treated plant sample indicates that the modified precursor has an effective antimicrobial property.

In another embodiment, the fibrous material is exposed to a peroxidase enzyme.

In yet another aspect of the instant invention, a method for increasing the amount of organic material in a plant that is resistant to degradation is provided. In one embodiment, the method comprises exposing at least a part of a plant to a preparation of a modified lignin precursor, wherein at least some of the preparation is taken up by the plant and wherein the modified lignin precursor is incorporated into a macromolecule of the plant.

In a preferred embodiment, the modified precursor is a monolignol containing an unnaturally-occurring chemical group. In a further embodiment, the monolignol is selected from the group consisting of courmaryl, coniferyl, and sinapyl or any one of their aldehyde or acid derivatives thereof. In yet another embodiment, therefore, a sinapate, ferulate, cinnamate, sinapoyl aldehyde, coniferyl aldehyde, or cinnamyl aldehyde precursor may be modified according to the instant method. In yet one other embodiment, the modified precursor may be a modified cinnamic acid molecule.

In a more preferred embodiment, the modified precursor may be any C6-C1, C6-C2 and C6-C3 molecule that contains an unnaturally-occurring chemical group or a naturally-occurring group at an unnatural position on the C6 aromatic ring. In one embodiment, the unnaturally-occurring chemical group may be a halogen, an amide, an amino, a nitro-group, a hydroxymethyl, a hydroxy, a sulfur and a methyl. In another embodiment, an "unnatural position" on the C6 aromatic ring may be any one of positions 1–6 that normally does not contain a naturally-occurring group.

In a more preferred embodiment, the modified precursor is a modified C6-C3 molecule. In another preferred embodiment, the modified C6-C3 molecule is a cinnamic acid-characterized molecule.

In a further aspect, the modified precursor is a mixture of at least any two of a para-coumaryl alcohol, a coniferyl alcohol or a sinapyl alcohol or their acid or aldehyde derivatives.

In yet another preferred embodiment, the macromolecule is a lignin or a lignincellulose.

One other aspect of the present invention relates to a method for making a lignin prodrug. In one embodiment, the method for making a lignin prodrug comprises administering a preparation of a modified precursor to at least a part of a plant; and growing the plant, wherein at least some of the preparation is taken up by the plant; and wherein the modified precursor is incorporated into a natural macromolecule of the plant.

In a preferred embodiment, the preparation is administered to at least a part of a plant, by at least one of a spray, an injection, an external application, or by a drench.

In another preferred embodiment, the plant is any lignin-producing plant or any lignin-containing plant. In a preferred embodiment, the plant is at the established growing phase of its developmental stage.

In yet another aspect, the present invention provides a method for screening a molecule containing an unnaturally-occurring chemical group for phytotoxicity. In one embodiment, the method comprises, treating a plant with a modified lignin precursor; detecting the extent of plant growth, or part thereof, wherein significant inhibition of growth of the plant, or part thereof, indicates that the modified lignin precursor is phytotoxic.

In another embodiment, any observable characteristic, trait or phenotype of a plant treated with a modified precursor may be monitored. Thus, in one preferred embodiment, the color of the plant may be monitored. In another preferred embodiment, the qualities of the wood, such as texture, color, hardness and the like, are altered by treating the plant with a modified precursor. In a preferred embodiment, the plant is any lignin-containing plant.

In a preferred embodiment, the modified precursor is a monolignol containing an unnaturally-occurring chemical group. In a further embodiment, the monolignol is selected from the group consisting of courmaryl, coniferyl, and sinapyl or any one of their aldehyde or acid derivatives thereof. In yet another embodiment, therefore, a sinapate, ferulate, cinnamate, sinapoyl aldehyde, coniferyl aldehyde, or cinnamyl aldehyde precursor may be modified according to the instant method. In yet one other embodiment, the modified precursor may be a modified cinnamic acid molecule.

In a more preferred embodiment, the modified precursor may be any C6-C1, C6-C2 and C6-C3 molecule that contains an unnaturally-occurring chemical group or a naturally-occurring group at an unnatural position on the C6 aromatic ring. In one embodiment, the unnaturally-occurring chemical group may be a halogen, an amide, an amino, a nitro, a hydroxymethyl, a hydroxy, a sulfur and a methyl. In another embodiment, an "unnatural position" on the C6 aromatic ring may be any one of positions 1–6 that normally does not contain a naturally-occurring group.

In a more preferred embodiment, the modified precursor is a modified C6-C3 molecule. In another preferred embodiment, the modified C6-C3 molecule is a cinnamic acid-characterized molecule.

In a further aspect, the modified precursor is a mixture of at least any two of a para-coumaryl alcohol, a coniferyl alcohol or a sinapyl alcohol or their acid or aldehyde derivatives.

In one other aspect of the instant invention, an activated lignin antimicrobial preparation is provided. In one embodiment, these lignin-derived molecules comprise an unnaturally-occurring chemical group selected from the group consisting of a halogen, an amide, an amino, a nitro-group, a hydroxymethyl, a hydroxy, a sulfur and a methyl. However, the present invention is not limited to the use of only these chemical groups. Other chemical groups may be added to either the aromatic or aliphatic portions of a precursor molecule according to the instant invention.

In yet another aspect, a method for reducing microbial activity in soil is provided. In a preferred embodiment, this method comprises applying the activated lignin antimicrobial preparation to the soil. In one embodiment, the preparation is applied by at least one of a spray, injection, external application, or a drench.

In yet one more aspect, a method for changing at least one characteristic of a lignin-containing plant is provided. Accordingly, the method comprises treating a plant with a modified lignin precursor and growing the plant and noting the change in any characteristic of the plant. In one embodiment the modified lignin precursor is applied by a spray, an injection, an external application, or a drench to the plant.

In a preferred embodiment, the characteristic of the plant that is changed is any one of texture, color, or hardness of the plant or any plant-derived materials. In a preferred embodiment, any one of texture, color or hardness of wood is altered by the application of a modified precursor to the plant. Thus, in another embodiment, any plant-derived material that is derived from a plant that has been treated with a modified precursor of the present invention may be changed according to the instant method.

In yet another aspect, a synthetically-made lignin prodrug comprising at least one of a modified C6-C1, a C6-C2 or a C6-C3 molecule is provided. In a preferred embodiment, the C6-C1, a C6-C2 or a C6-C3 comprises an unnaturally-occurring chemical group. In another embodiment, the unnaturally-occurring chemical group is selected from the group consisting of a halogen, an amide, an amino, a nitro, a hydroxymethyl, a hydroxy, a sulfur, and a methyl. In another preferred embodiment, any unnaturally-occurring chemical group may be added to the C6 aromatic ring.

The present invention also provides a lignin-containing plant that comprises a modified precursor. In one embodiment, the modified precursor is incorporated into a biochemical pathway. In a further preferred embodiment, the biochemical pathway is the lignin biosynthetic pathway. In yet another embodiment, the modified precursor is incorporated into a plant lignin macromolecule. In yet another preferred embodiment, the modified precursor becomes a part of a lignin degradation product. In yet one more embodiment, the lignin-containing plant may be an angiosperm or a gymnosperm. In another preferred embodiment, the plant may be any crop.

In a further embodiment, the modified precursor that is in the lignin-containing plant is at least one of a modified C6-C1, a C6-C2 or a C6-C3 molecule. In a preferred embodiment, these aromatic molecules may comprise an unnaturally-occurring chemical group. In a preferred embodiment, the unnaturally-occurring chemical group is selected from the group consisting of a halogen, an amide, an amino, a nitro, a hydroxymethyl, a hydroxy, a sulfur, and a methyl.

In any one of the above embodiments, the modified precursor may be applied to a plant in a formulation, wherein the formulation contains another compound or chemical. In a preferred embodiment, the formulation contains a herbicide. In a more preferred embodiment, the herbicide is glyphosate. In another preferred embodiment, the formulation contains a plant growth regulator. In a more preferred embodiment, the plant growth regulator is glyphosine.

In one aspect, the present invention provides a method for identifying a fungicide that prolongs the degradation of a plant. In one embodiment, this method comprises administering to the plant a fungicidal candidate, harvesting the plant and monitoring the rate of degradation of the plant in comparison to an untreated plant of the same species. In another embodiment, the fungicidal candidate may be administered any time up to harvesting or death of the plant. Thus, in yet another embodiment, the inventive method encompasses treating a living or non-living plant with a fungicide. In another embodiment, a slower rate of degradation in the treated plant indicates that the fungicidal candidate is a candidate that prolongs the degradation of the plant. In yet another embodiment, the step of treating a living or non-living plant with a fungicidal candidate is performed by spraying, injecting, externally applying, or drenching. In one other embodiment, the fungicidal candidate is administered at a rate of approximately 100 ppm (parts per million) on a weight basis of the weight of the plant. Any rate of administration can be used. For instance, the rate of administration may be 1 ppm–10 ppm–50 ppm, 60 ppm, 70 ppm, 80 ppm, 90 ppm, 100 ppm, 200 ppm, 300 ppm, 400 ppm, 500 ppm, 1000 ppm, 5,000 ppm, 10,000 ppm, or more than 10,000 ppm. A fungicidal candidate that prolongs the degradation of a treated living or non-living plant in comparison to an untreated living or non-living plant is a suitable fungicide for use in increasing the sequestration of carbon.

Thus, another aspect of the invention envisions a method for increasing the sequestration of carbon in a non-living plant biomass. This method comprises administering to a living or non-living plant a fungicide. In one embodiment, the fungicide may be applied to a living plant before the plant is harvested. In one embodiment, administration of the fungicide prolongs the rate of degradation of the plant, thereby increasing the sequestration of carbon in the non-living plant biomass. In another embodiment, the fungicide is administered 4 weeks before harvesting the plant. In yet another embodiment, the fungicidal candidate is administered at a rate of approximately 100 ppm on a weight basis of the weight of the plant. In one more embodiment, the step of treating a living or non-living plant with a fungicidal candidate is performed by spraying, injecting, externally applying, or drenching.

The present invention encompasses any compound, chemical, or modified macromolecule precursor, identified by the inventive, or another, screening method, that is useful in retarding degradation of plant organic materials. Thus, the present invention encompasses treating a plant with any chemical that is specifically applied to slow down plant degradation.

DETAILED DESCRIPTION OF THE PREFERRED EMBODIMENTS

The present invention provides an inexpensive, quantifiable, and reversible method for increasing the resistance of terrestrial organic materials to biodegradation. Furthermore, when the inventive organic materials do decompose, they are toxic to the microorganisms in the local environment that bring about that degradation. Thus, the present invention slows down the rate at which plant materials are degraded in soil organic materials. Accordingly, the inventive organic compositions and methods, conveniently and effectively sequester carbon and photosynthetically-fixed carbon.

Specifically, the methods described herein modify one or more constituents of plant macromolecules so that the macromolecules are more resistant to degradation, and also more toxic to degradative microorganisms when they are broken down and decompose. Incorporating modified, non-phytotoxic chemical precursors of macromolecules into plants to retard environmental and microbial degradation of those plants, for example, is one way in which the present invention enhances the sequestration of carbon. According to the present invention, a modified, non-phytotoxic chemical precursor is also referred to as a "molecule" used to treat a plant or part thereof. Thus, the term "molecule" comprises a modified precursor, such as of a plant macromolecule like ligin and cellulose, as well as other moitieties that can be used to introduce an unnaturally-occurring chemical group into the structure of an indigenous plant macromolecule.

Thus, another method for sequestering carbon provided by the present invention is by treating living and non-living plants with fungicides. The fungicidal chemicals also can be used to retard degradation and increase toxicity of the plant degradation products by becoming incorporated into macromolecules of a plant treated with the fungicide.

The present invention uses terms and phrases that are well known to those practicing the art. Unless defined otherwise, all technical and scientific terms used herein have the same meaning as commonly understood by one of ordinary skill in the art to which this invention belongs. Generally, the nomenclature used herein and the chemical laboratory procedures described herein are those well known and commonly employed in the art. Standard techniques are used for analytical chemistry, organic synthetic chemistry, chemical syntheses, chemical analysis, and formulation and delivery. Generally, enzymatic reactions and purification and/or isolation steps are performed according to the manufacturers' specifications.

Antimicrobial molecule: As used herein, an "antimicrobial molecule" is a substance, compound or chemical that is capable of destroying or inhibiting the growth of an microorganism. Thus, an "antimicrobial molecule" may also be described as a microbial-specific, or a bacterial-specific, toxin. Examples of such molecules include halophenol- and bis-phenol-based antimicrobials.

Bagasse: The dry, fibrous residue remaining after the extraction of juice from the crushed stalks of a plant, such as sugar cane.

Chemical group: A chemical group may be a halogen, an amide, an amino, a nitro, a hydroxymethyl, a hydroxy, a sulfur, a phenyl or a methyl group that can be substituted at one of the carbon positions of a precursor molecule, such as at a carbon of a monolignol precursor. However, the invention is not limited to the use of only these chemical groups. Other chemical groups known to those in the art may be similarly employed in the fashion of the instant invention.

Degradation: As used herein, "degradation" refers to the breakdown, decomposition or deterioration of an organic material, such as plant- or soil-organic matter, like lignin, into discreet degradation products. Degradation may be facilitated by environmental conditions, chemical attack or by the activity of microorganisms upon such organic material.

Degradative microorganism: A "degradative microorganism" may be a fungus, such as a white-rot fungus or a wood-rotting fungus, or any bacterial species or actinomycetes species. A plant "pathogen" may be considered a degradative organism.

Degradation product: A degradation product is produced from the breakdown of organic material by any one of a number of factors, such as in an oxidizing environment or microbial activity. The organic material may be derived from a plant molecule. Furthermore, in the context of the instant invention, degradation products may possess different or enhanced properties as compared to the whole, base substance of which they comprise, due to the incorporation of unnatural chemicals or molecules that become activated upon the creation of degradation products. Thus, a degradation product of the present invention may possess enhanced antimicrobial properties, when the molecule from whence it came is degraded. A part of a plant lignin molecule that is created in vivo, or that is made synthetically in vitro, may be considered a degradation product.

Lignin: Lignin is a water insoluble polymer primarily responsible for the rigidity of plant stems. The macromolecule serves as a matrix around the polysaccharide components of some plant cell walls. For instance, some tree species synthesize large quantities of lignin, with lignin constituting between 20% to 30% of the dry weight of wood. Lignin also plays a role in disease resistance of plants by impeding the penetration and propagation of plant pathogens and degradative microorganisms.

Lignin precursor: A "precursor" molecule that is part of the lignin biosynthetic pathway is a "lignin precursor." See the definition of a "precursor" below.

Lignin-derived molecule: A "lignin-derived molecule" may be a degradation product of a plant lignin macromolecule or any composite molecule thereof.

Macromolecule: A macromolecule as used herein refers to a plant-derived polymer such as lignin and lignincellulose.

Modified lignin precursor: A "modified lignin precursor" contains an unnatural substitution at any one of its carbons. The so-called "modified precursor" (see definition below) may be incorporated into lignin, either by natural or synthetic pathways, and may be a monolignol, or acid, or aldehyde, derivative of a monolignol.

Modified precursor: Any "precursor," as defined below, that is involved in the formation of a macromolecule or is any derivative of a biochemical pathway that results in the creation of a macromolecule may be considered a "precursor." One such macromolecule is lignin. As such, any one of these precursors may be modified in the manner according to the present invention and incorporated into a biochemical pathway to alter the properties of the resultant macromolecule. To this end, a "modification" may include the addition of a chemical group that is not normally bound to the aromatic ring of a precursor molecule. A "modification" also may encompass the positioning of a chemical group that is normally associated with a precursor onto a different, or onto multiple carbons, of a precursor aromatic ring, and/or the aliphatic portion of the molecule. Any halogen, for instance, may be added to a precursor molecule so as to "modify" the precursor. Any "unnaturally-occurring" chemical group may be added to a precursor also. See definition below for "unnaturally-occurring."

Molecule comprising a modified precursor: A molecule that contains a modified precursor may be a plant-derived, macromolecular structure or a part thereof, such as lignin, or lignincellulose complex, or a degradation product of a macromolecular structure.

Molecule containing an unnaturally-occurring chemical group: Plant materials such as lignin and lignincellulose may be modified so as to contain chemical groups that are not normally present in such macromolecules. Those chemical groups can be a part of a molecule that is applied to a plant or part thereof. Preferably, the molecule comprising the chemical group that does not naturally occur in the plant, becomes assimiliated in a biosynthetic pathway in the plant, and ultimately incorporated into a plant macromolecule. Thus, those materials become "unnatural." For instance, examples of "unnaturally-occurring chemical groups" not naturally found in lignin, include, for instance, a halogen, an amide, an amino, a nitro, a hydroxymethyl, a sulfur group, a hydroxy group and a methyl.

Monolignol: A "monolignol" is one of three molecules that eventually become incorporated into lignin. These molecules are p-courmaryl, coniferyl, and sinapyl.

Plant-derived: "Plant-derived" means any substance, chemical, polymer or molecule that is produced by a plant, or that is normally contained within a plant. Thus, a lignin molecule produced by a plant is "plant-derived," as well as a lignin molecule synthetically made in vitro.

Plant organic matter: Any molecule of a plant that contains a carbon may be regarded as "plant organic matter."

Lignin is a "plant organic matter." When a plant becomes degraded, however, the plant organic matter may become "soil organic matter."

Precursor: A "precursor" includes any C6 aromatic ring compound that contains a one, two or three carbon aliphatic chain, wherein the terminal carbon of that chain is an acid, an aldehyde or an alcohol. For instance sinapate, ferulate, cinnamate, sinapoyl aldehyde, coniferyl aldehyde, cinnamyl aldehyde, sinapoyl alcohol, coniferyl alcohol, cinnamyl alcohol, and cinnamic acid are precursors that may be modified according to the instant invention. Thus, natural precursors of lignin may be a 4-hydroxy- C6-C3 molecule, such as coumaryl; a 3-methoxy-4-hydroxy- C6-C3 molecule, such as ferulic; or a 4-hydroxy-3,5-hydroxymethyl C6-C3 molecule, such as synapic acid. A modified precursor can be any C6-C1, C6-C2 and C6-C3 molecule that contains an unnaturally-occurring chemical group, like a chlorine, or a naturally-occurring group in an unnatural position on the aromatic ring of a C6 molecule and/or on its aliphatic carbon portion. Examples of such precursors include the lignin-pathway monolignols, as defined above. Indeed, any of the aromatic ring compounds in the lignin-biosynthetic pathway may be modified according to the instant invention. Accordingly, any chemical that is characterized by a C6-C3 base, i.e., a cinnamic acid or a phenylpropanoid base, is a precursor that can be modified according to the instant invention. In similar fashion, any C6-C2- or a C6-C1-based chemical is a precursor that may be modified according to the instant invention.

Preparation of modified precursor: A modified precursor "preparation" is a formulation suitable for administering to terrestrial ecosystems or individual plants. Thus, a "preparation of modified precursor" may be a solution, a powder, a solid, a gel or a vapor.

Prodrug: As used herein, a "prodrug" is an inactive version of a chemical moiety that is converted into its active form by environmental or degradative microorganism-driven processes. In the context of the instant invention, a lignin molecule that contains a modified precursor molecule is a "prodrug" because its degradation products possess antimicrobial properties.

Soil organic matter: All dead, or biologically derived organic material, in or lying on the soil, that contain carbon is referred to herein as "soil organic matter."

Synthetically-made: "Synthetically-made" refers to the in vitro synthesis of a molecule by, for example, standard chemical methods. A lignin molecule that is made chemically, for instance, outside of a plant may be considered "synthetically-made." Furthermore, a lignin molecule that is made by recombinant methods also may be considered "synthetically-made." To this end, a lignin gene that has been recombinantly manipulated, such as to contain a genetic mutation, also is considered to be "synthetically-made" according to the instant invention.

Toxicity: As used herein, "toxicity" relates to producing a toxic effect on cells. Thus, "toxicity" refers to the ability of a lignin-derived plant molecule, for example, to destroy or inhibit the growth of a microorganism. Preferably, such a molecule is not toxic to the plant within which it resides.

Unnaturally-occurring: A precursor, or a C6-C3 cinnamic acid, or any phenylpropanoid base, may be "unnaturally-occurring" if such a molecule contains a chemical group that is not normally a part of that precursor, or is located in a position that is different to its normal position on the C6 aromatic ring or the associated aliphatic carbon chain. In one embodiment, these lignin-derived molecules comprise an unnaturally-occurring chemical group selected from the group consisting of a halogen, an amide, an amino, a nitro, a hydroxymethyl, a hydroxy, a sulfur and a methyl. However, the present invention is not limited to the use of only these chemical groups. Other chemical groups may be added to either the aromatic or aliphatic portions of a precursor molecule according to the instant invention. Thus, unnatural precursors can be those C6-C3 molecules that include additional chemical groups or chemical groups that are positioned elsewhere on the C6-C3 molecule. Thus, a chlorine, or any halogen, that is substituted on to a naturally-occurring monolignol renders that monolignol as an "unnaturally-occurring" precursor. Accordingly, an unnaturally-occurring precursor may be any C6-C3, C6-C2, C6-C1 molecule that is not a natural precursor. See definition of "precursor" above for examples of "naturally-occurring precursors."

Aspects of the Instant Invention

The inventive methods strengthen and protect plant macromolecules against microbial and environmental degradation by incorporating non-phytotoxic molecules into various macromolecular structures of the plant. Consequently, the rate of decomposition of organic materials containing the inventive molecules is reduced, and therefore the rate at which carbon is released into the atmosphere, also is reduced. Accordingly, the inventive molecules contribute to the sequestration of carbon in the terrestrial plant biomass.

A molecule of the present invention may be a component of a biosynthetic pathway that produces a plant macromolecule. Thus, a molecule may be a macromolecule "precursor" that is modified, taken up by the plant, and incorporated into the relevant biosynthetic pathway. Accordingly, the macromolecule produced from such a pathway would contain chemical elements of the modified precursor in its structure. For example, a chemical group that does not naturally occur in the plant may be incorporated into the molecular structure of a macromolecule in the plant by administering a macromolecule precursor that contains the desired chemical group.

Similarly, known chemicals, such as fungicides, can be applied to a plant and ultimately incorporated into a plant's biomass, to enhance a plant's resistance to degradation, toxicity to microorganisms, and improved carbon sequestration.

Thus, the present invention produces plants that take a longer time to decompose and creates plant degradation products (hereafter, "prodrugs"), that more effectively inhibit or destroy degradative microorganisms. Indeed, upon catalyzing the enzymatic breakdown of a plant material, the degradative microorganisms unwittingly activate the prodrugs, which kill, inhibit, or slow the degradative activity of those microorganisms.

Any plant may be treated according to the methods of the present invention, including gymnosperms, angiosperms, dicotyledonous plants and monocotyledonous plants. A gymnosperm is a plant, such as a cycad or conifer, whose seeds are not enclosed within an ovary. An angiosperm, on the other hand, is a flowering plant whose ovules are enclosed in an ovary. In this respect, a "dicot" is a flowering plant whose embryos have two seed halves or cotyledons. Dicotyledonous plants may be treated with fungicide and include, but are not limited to, tobacco, tomato, potato, sweet potato, cassaya, legumes including alfalfa and soybean, carrot, strawberry, lettuce, oak, maple, walnut, rose, mint, squash, daisy, and cactusa. A "monocot" is a flowering plant whose embryos have one cotyledon or seed leaf. Examples of monocots include, but are not limited to, turf grass, maize, rice, oat, wheat, barley, sorghum, orchid, iris, lily, onion, and palm.

(i) Modified Lignin Precursor Molecules Retard Plant Degradation and Increase the Toxicity of Degradation-Activated Lignin Prodrugs Of all the macromolecules present in such plant organic material, lignin is by far the most abundant and hardy, and, therefore, is a prime candidate for modification according to the strategies of the present invention. It is the degradation of lignin that largely determines the rate and timing of the decay of soil organic materials and, thus, the rate of release of carbon. Thus, the rate at which lignin is degraded is proportionate to the rate at which gaseous carbon is returned to the atmosphere. Slowing down the rate of lignin degradation will also reduce the rate at which carbon is liberated from decaying plants, and thereby increase carbon sequestration.

Figure 1:
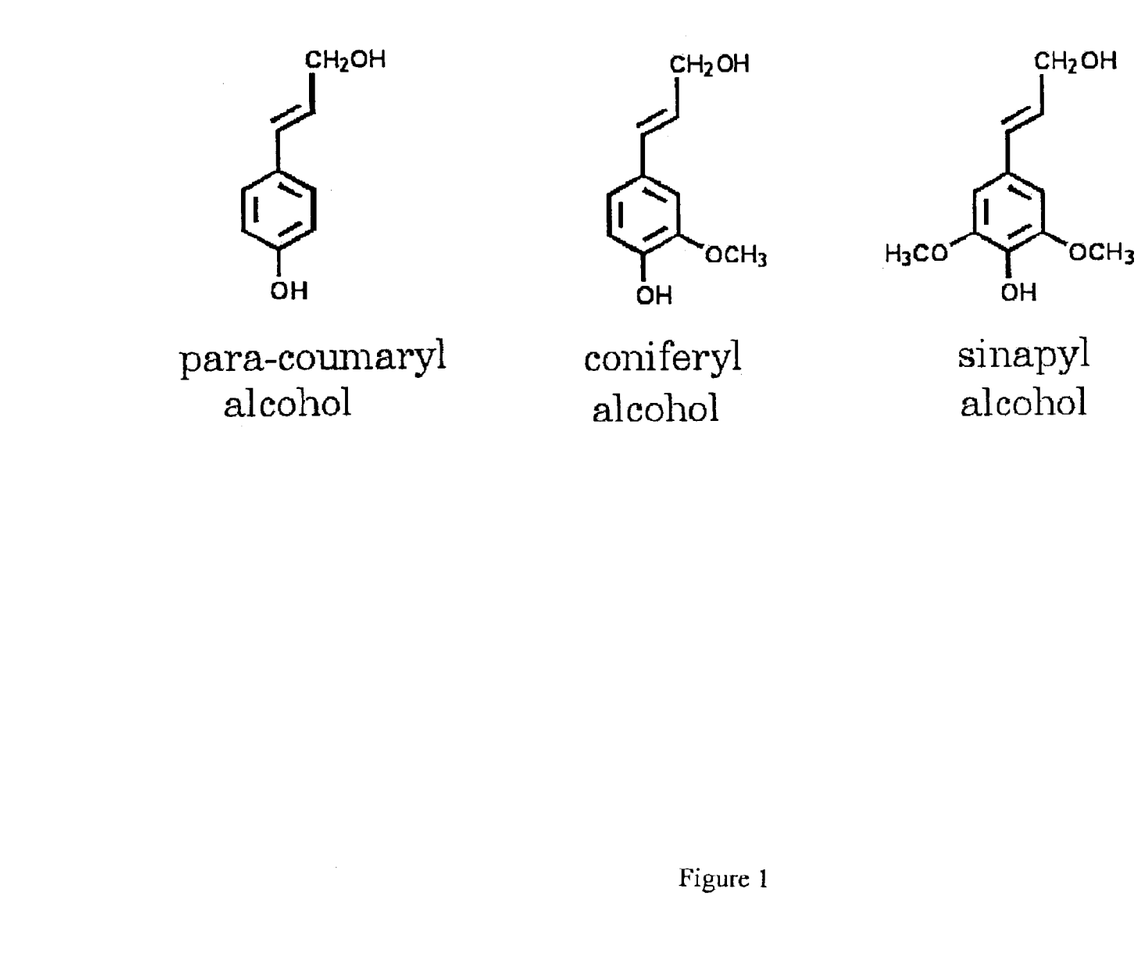
FIG. 1 shows the chemical structures of lignin monolignol precursors, para-coumaryl alcohol, coniferyl alcohol and sinapyl alcohol.
Figure 2:
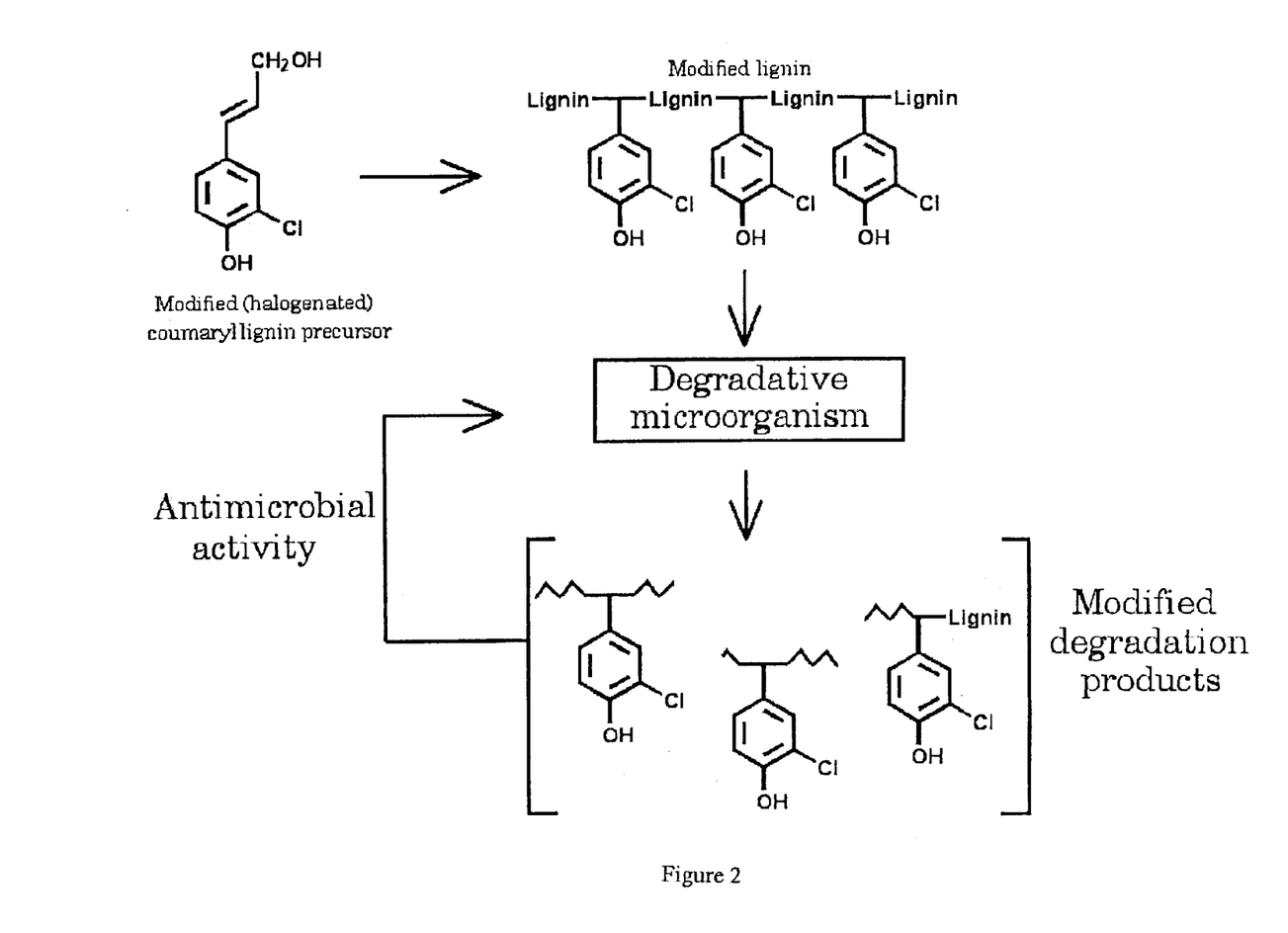
FIG. 2 is a schematic diagram showing the incorporation of a modified lignin precursor (halogenated coumaryl) into a lignin macromolecule and the subsequent generation of lignin degradation products after microbial activity upon the lignin. The degradative lignin products have enhanced anti-microbial activities that inhibit or destroy the degradative microorganism.

The lignin biosynthetic pathway is elaborate and culminates in the conversion or incorporation of monolignol precursor molecules into lignin and non-lignin macromolecular structures by various enzymes. See, for instance, FIG. 2, at page 1003 of Whetten et al., *The Plant Cell*, 7, 1001–1013, 1995, which is incorporated by reference herein. For example, phenylalanine ammonia lyase converts phenylalanine into the monolignol precursor, cinnamic acid, and tyrosine ammonia lyase converts tyrosine into p-coumaric acid. Thus, para-coumaryl alcohol, coniferyl alcohol, and sinapyl alcohol are all examples of lignin monolignols, which become para-hydroxyphenyl residues, guaiacyl residues, and syringyl residues respectively when incorporated into the lignin polymer.

Many of lyase enzymes do not distinguish between chemically diverse C6-C3 substrates. Accordingly, many different types of C6-C3 precursors can easily become covalently incorporated into lignin aromatic polymers. See, for instance, Kirk et al., Chapter 4, at page 77 of LIGNIN BIODEGRADATION, Volume 1, which describes the incorporation of $^{14}C$ labeled lignin precursors into lignin.

Such "incorporation" is made possible through a variety of chemical reactions, such as dehydrogenative polymerization, oxygen radical-mediated coupling, and esterification, which link together the monolignols to form the larger lignin macromolecule. The random nature of the inter-monolignol linkages results in extensive heterogeneity of the lignin macromolecule. Accordingly, the constituency of the resultant lignin macromolecule is largely determined by the amounts and types of individual monolignol and related precursors that are available at the assembly site during the lignification process. Variations in lignin composition between species as divergent as gymnosperms, angiosperms and grasses, appear to be due to the relative rates of biosynthesis and the amounts of specific monolignol or other precursors that are present during lignification.

It follows, then, that treating plants with a specific precursor molecule will result in the incorporation of the precursor into a variety of different biochemical pathways, including the lignin biosynthesis pathway, and the formation of modified plant material.

Therefore, one aspect of the invention involves treating plants with any one of a number of lignin precursor molecules that are designed and screened for their ability to retard biodegradation. Furthermore, the modified precursors are also selected for their ability to impart enhanced antimicrobial properties upon plant degradation products, when attacked by environmental and microbial factors.

To this end, the present invention incorporates phenylpropanoid acid, aldehyde and alcohol lignin precursors that are not naturally produced by plants, into organic macromolecules like lignin and cellulose. These precursors can be produced synthetically and can be designed to contain substitutions in the C6 aromatic portion or in the C3 propanoid portion, or in both portions, of such a C6-C3 molecule. The substitutions to the phenylpropanoid lignin precursor can be of any sort and are well known in organic chemistry. For instance, a halogen, an amide, an amino, a nitro, a hydroxymethyl, a hydroxy, and methyl groups can be substituted into a C6-C3 molecule. It is also possible to introduce other groups at different positions of these precursor molecules.

In particular, halogen-substituted cinnamic acids can be used as the synthetically produced and unnatural C6-C3 phenylpropanoid lignin precursors. Thus, a chlorine, bromine or fluorine may be incorporated into a lignin precursor.

There is a wide-range of halogenated, cinnamic acids that are commercially available and inexpensive. Many of these substituted cinnamic acids are not phytotoxic. Many of them are taken up by plant tissues when applied as a spray, a drench or an injection and a number of the halogen-substituted cinnamic acids can be incorporated by plants into lignin polymers. Additionally, they can be employed either individually or in combination as required. Although halogen-substituted cinnamic acids do appear to be converted to the corresponding monolignol lignin precursor and incorporated into lignin, they do not appear to be catabolized or degraded by the plants that have acquired and incorporated these synthetic chemical precursors.

Plants also may be treated with C6-C1 molecules, such as benzoic or benzyl acid or C6-C2, phenylacetic or phenylacetyl acids, aldehydes and alcohol compounds that are not naturally produced by plants.

Thus, a preparation, such as a liquid solution, of modified precursors can be applied to a plant via injection, external application, sprays or by drenching the roots. The treated plants can be any plant, such as an angiosperm or gymnosperm. The plant preferably comprises lignin or a lignin-based compound.

Enough is known of the monolignol composition of many terrestrial systems that it is possible to select a specific monolignol precursor for modification purposes. For instance, it is known that softwood lignins are primarily made up of coniferyl alcohol, whereas hardwood and non-woody plants, such as forage grasses and legumes, are made from a mixture of coniferyl and sinapyl alcohols.

Furthermore, a plant can be selected at an appropriate developmental stage for successful uptake of modified precursors, as well as the subsequent formation of macromolecules such as lignin that contain those precursors. To this end, "established growing plants" are of a suitable stage in development for use in the context of the instant invention.

The modified precursors can be produced synthetically and designed to contain substitutions in the C6 aromatic portion, or in the C1 or C2 aliphatic portion, or in both aromatic and aliphatic portions of the molecule. Again, the substitutions can be of any sort and are well known in organic chemistry. The compounds can often be taken up by treated plants and then may be incorporated into lignin polymers. These events result in lignin materials that are chemically distinct yet functionally similar to natural lignin.

Thus, similar to halogenated cinnamic acid, one also may use halogen-substituted benzaldehyde compounds as synthetically produced and unnatural C6-C1 compounds. There is a wide-range of halogenated benzaldehydes that are both commercially available and inexpensive. Some of these substituted benzaldehydes are not phytotoxic while others are phytotoxic (and potentially herbicidal), and many of them are taken up by plant tissues when applied as a spray, a drench or an injection. Additionally, they can be employed either individually or in combination as required. A rapid screening of these compounds can determine which of these compounds are phytotoxic and hence are not appropriate for use in this technology.

Specifically, these modified lignin precursors can be easily screened for phytotoxicity and increased resistance to microbial degradation. The modified precursors may be screened as well as the degradation products of the macromolecule of which they comprise.

The present invention is not limited to the use of only lignin precursors or the precursors specifically described herein. Any molecule, compound, or chemical that becomes incorporated into a plant macromolecule can be modified according to the regimes described herein. Thus, any molecule that is a part of a plant biosynthetic pathway, such as the lignin biosynthetic pathway, may be modified according to the inventive methods and used as prescribed. Any of the molecules described, for instance, in Whetten et al., supra, can be modified according to the present invention.

(ii) Fungicides also can be Incorporated into Plant Macromolecules to Retard Plant Degradation and Enhance Prodrug Toxicity The present invention also contemplates the use of fungistatic and fungicidal chemical agents (i.e., "fungicidal candidates") to sequester carbon in terrestrial ecosystems. Examples of fungicidal candidates include thiabendazole (2-(4-thiazolyl)benzimidazole)), carbendazim (methyl-2-benzimidazole carbamate) and propiconazole (1-[[2-(2,4-dichlorophenyl)-4-propyl-1,3-dioxolan-2-yl] methyl]-1H-1,2,4-triazole); as well as other commercially known fungicides, such as benomyl, captan, chlorothalonil, copper, Liquid Copper, mancozeb, maneb, sulfur Lime sulfur, Liquid Sulphur, triforine, Orthenex. The skilled artisan would know what fungicides are available to use in the method of the present invention. For example, see the description of various fungicides in the "Fungicide Kit" (catalog no. PSK-42) at page 118 of ChemService Inc.'s, PESTICIDE & METABOLIC STANDARDS CATALOG, which is incorporated herein by reference. A fungicidal preparation administered to a plant may comprise one or more fungicides.

As is well known, one function of a fungicide is to eradicate and/or inhibit the growth and proliferation of fungi and pathogens that attack and live off plants. The ultimate purpose of a fungicide is to protect living plant materials against pathogenic attack and against plant biomass biodegradation. There have no reports, however, of the use of fungicides in planta against non-pathogenic saprophytic soil microorganisms. Furthermore, there have been no reports of the role of fungicides in promoting carbon sequestration by protecting lignin and lignocellulose biomolecules according to the spirit of the present invention. Thus, the present invention envisions the use of fungicides to prolong the degradation non-living plant biomass.

Accordingly, the present invention provides a method for identifying which fungicidal chemicals, i.e., fungicidal candidates, are useful for prolonging the degradation of harvested plant materials. The skilled artisan knows that "harvest" means the act or process of gathering a crop, tree, plant, bush or other plant material. Thus, a harvested plant is one that is non-living. "Non-living" applies, in general, to whatever once had, but no longer has, physical life. Accordingly, the inventive method encompasses the administration of a fungicide to (i) a living plant that is naturally near-death; (ii) to a non-living plant; or (iii) to a living plant that is to be deliberately harvested. In this respect, a plant of any age or stage of development can be treated according to the present invention. For instance, a fungicide may be applied to a diseased plant, to a dead plant or to a plant that is to be harvested. By applying the fungicide in any one of these contexts, one may purposely slow down the rate of degradation of the non-living plant.

Thus, in determining a suitable fungicide for use in prolonging degradation of a plant, the inventive method involves administering to a plant a fungicidal candidate, harvesting the plant and then monitoring the rate of degradation of the plant in comparison to an untreated plant of the same species. The inventive method also encompasses administering to a near-death or non-living plant a fungicidal candidate and then monitoring the rate of degradation of the plant in comparison to an untreated plant of the same species.

The fungicidal candidate can be applied according to any standard techniques, such as by spraying, injecting, externally applying, or drenching. Any amount of fungicidal candidate may be applied when identifying which fungicidal candidates are useful for prolonging the rate of plant degradation. For instance, the fungicidal candidate could be administered at a rate of approximately 100 ppm on a weight basis of the weight of the plant. The fungicidal candidate may be administered to a plant at any time, and at multiple times, before the plant is harvested. By monitoring the level of degradation of the treated plant in comparison to an untreated plant the skilled artisan can readily determine the effects of the fungicidal candidate upon prolonging the rate of plant degradation. The skilled artisan would know how to monitor the level of plant degradation. For instance, the artisan may record the staining intensity of lignin over time, wherein a reduced lignin staining intensity over time indicates plant degradation.

Accordingly, once a fungicidal candidate has been found to prolong plant degradation, one may apply that fungicide to other plants of the same or different species. Thus, the present invention envision the application of fungicidal preparations to plants, before they are harvested, so that the rate of their degradation after harvest is prolonged.

(iii) The Present Invention Increases the Toxicity of Degradation-Activated Lignin Prodrugs The degradation products of macromolecules synthesized with the inventive precursors are referred to herein as "prodrugs" because the degraded macromolecules containing the introduced chemical groups become very potent when exposed. The prodrugs are highly phenolic and enhance the antimicrobial properties naturally associated with lignin degradation products. Thus, the presence of such degradation products in soil retards lignin biodegradation. The rate of lignin biodegradation, and hence the amount of carbon sequestered in soils, is therefore related to the effectiveness of these antimicrobial compounds.

An increase in the potency of the lignin antimicrobial prodrugs more effectively inhibits or delays the metabolic activities of microbial species capable of degrading lignin. An increase in the effective lifetime of these degradation products would, therefore, confer longer times for complete lignin degradation and release of carbon.

Degradation of a modified lignin macromolecule formed with a halogen-substituted precursor, for instance, would produce a variety of antimicrobials, including halophenol and bis-phenol type degradation products. Halogen-substituted phenolic compounds and bis-phenol molecules are highly active against both bacterial and fungal species.

The bis-phenols are hydroxy-halogenated derivatives of two phenolic groups connected by various bridges. Additionally, catabolism of these compounds will potentially release toxic metabolic intermediates such as fluoroacetic acid within the degradative microorganisms.

The lignase peroxidase enzymes produced by white-rot fungi to bring about such catalysis, are low molecular weight enzymes that produce oxygen radicals to destroy lignin. The peroxidases depolymerize lignin to produce moieties that are more rapidly assimilated by white-rot fungi and other soil microbes than non-oxidized monomeric aromatic analogues.

The degradation moieties are heterogeneous and contain one or many low molecular weight hydroxy- or hydroxymethyl-substituted aromatic ring moieties. These products are more soluble and accessible to a wide range of soil- and litter-dwelling fungi and bacteria. Soil microorganisms are able to incorporate these low molecular weight aromatic compounds and are able to further degrade, catabolize and utilize these products as carbon sources for respiration and growth. The activity of such enzymes, however, would also expose such microorganisms to the toxic phenolic prodrugs of the present invention.

Accordingly, the present invention also improves the quality of soil by increasing its content of carbon-containing organic matter. Incorporation of such treated plant biomass into the soil will decrease the metabolic activity of lignin- and lignocellulose-degrading microorganisms, resulting in enhanced soil characteristics.

The rate and extent of lignin degradation by fungal microbes, such as the white-rot fungus, can be regulated by varying the amount of the modified precursor that is taken-up by the plant. Thus, degradation of plant organic materials by degradative microorganisms can be slowed down by regulating the dosage and timing at which modified lignin precursors are provided to the plant. Furthermore, by modulating the amount of modified precursor, such as a halogenated cinnamic acid, that is applied to a plant, one may modulate the concentration of chlorine that is eventually introduced into the environment in soil organic matter containing lignin and lignin degradation products. Thus, the chlorination, for instance, of plant organic materials is controllable.

The present invention reveals that an improved resistance to degradation due to treatment with a modified lignin precursor can be achieved in situ as well as in vitro. In both sugar cane and corn, treatment with a modified precursor, such as a halogen-substituted cinnamic acid or a benzaldehyde, increases biodegradative-resistance properties of plants in situ.

(iv) Additional Molecules for Use in the Present Invention

Modulators of aromatic biosynthesis also can be used in conjunction with a modified lignin precursor to enhance the biodegradative-resistance properties of a treated plant. Similarly, other herbicides, such as glyphosate, herbicide safners and plant growth regulators, such as glyphosine, are shown in the present invention to further enhance the degradation-resistant properties of modified lignin precursors.

(v) Assays for Determining the Effect of Modified Molecules Upon Plants and Degradative Microorganisms Treating plants with a modified precursor, such as with a halogen-substituted cinnamic acid, does not inappropriately affect the intensity of lignin. Hence, a conventional method for estimating relative amounts of lignin content by observing lignin staining intensity can be used to monitor the effect of a modified precursor upon lignin content and degradation. Thus, an increase or decrease in staining intensity may reflect an equivalent increase or decrease in the amount of lignin present in a plant biomaterial.

The staining intensity of lignin can be recorded visually according to an arbitrary scale, i.e., from 1 to 9 where a "9" indicates the strongest staining. Alternatively, the intensity of lignin staining between control and treated samples can be quantified using a photometer.

The Minimal Inhibitory Concentration (MIC) assay also may be employed to determine the capacity of a modified precursor-containing molecule to inhibit or slow down microbial growth. Thus, the MIC is another assay that may be used to determine the effects of a modified precursor on enhancing the antimicrobial properties of lignin degradation products.

Fungal growth, as determined by fungal hyphae mass, is retarded on bagasse treated with a modified precursor. Generally, reduced lignin stain intensity is associated with an increase in intensity of chitin stain, and by extrapolation, an increase in fungal biomass.

Other Applications

The environmentally harmful processes currently employed for treating lumber and wood products with toxic fungicidal agents to increase the useful lifetimes of such products can be avoided by use of the described methods. The methods result in more efficient production of ethanol and more efficient production of chemicals from plant sources and renewable feedstock.

Lignin, as well as other similar macromolecular polymers, can be made synthetically, obviating the need to grow plants for the purposes of investigating the effects of modified precursors on lignin structure and function. For some applications, increased lignin content is desirable since increasing the lignin content of a plant increases the mechanical strength of wood and may change its coloration, in addition to increasing its resistance to rot. Thus, synthetically-made lignin and enhanced lignin obtained from plant organic material can be used for a variety of purposes. For instance, a batch of lignin can be made using modified precursors to improve its degradation resistance and this used in the formulation of paints, building materials or wood products.

EXAMPLE 1

Plant Materials (i) Sugar cane: *Saccharum officinarum* L.: cv. B4362

Plants were cultivated in a greenhouse environment and modified precursors were applied via drench application to the roots. Prior to harvest plants were held in the dark for three days to reduce the starch content. Mature stalks were harvested, crushed, extracted and washed to remove the sugar and soluble materials. Bagasse was produced from the washed remaining solids for treatment and for subsequent staining and observation. Observations were made with a dissecting or a light microscope.

The production of bagasse is a routine procedure, well known to those in the art. Nevertheless, a short description of the method employed by the inventor follows. Approximately 50 g of sugar cane stalks were homogenized in a standard blender in approximately 4 to 5 volumes of water. The fibrous material obtained was strained and filtered, for example through cheesecloth, and the resultant material washed twice with water. This fibrous material was then processed again by blending in water, collected, and left to dry. The resultant fibrous material is bagasse. Accordingly, approximately 10–15 g of bagasse from 50 g of sugar cane stalks can be obtained using this method. Any bagasse samples referred to in the following Working Examples were produced according to this method.

(ii) Corn: *Zea mays* L.: Inbred Line B 73

Plants were cultivated in a greenhouse environment and modified precursors and control precursors were applied via a foliar spray. Treated plants were permitted to naturally mature, senesce and dry down. After dry down several centimeter long sections were taken from nodal and from internodal regions at the base of the stalk for further in situ soil treatment. After treatment, thin sections were made, stained and visually inspected. Observations were made with a dissecting or a light microscope.

EXAMPLE 2

Microbial, Soil and Chemical Materials (i) Microbial Materials

*Phanerochaete chrysosporium*, a lignin degrading fungus, was maintained on potato dextrose agar (PDA). Lignin degradation studies employed culturing the fungus in a liquid mineral salt medium that contained treated plant materials, such as bagasse from a plant that had been treated with a modified precursor preparation. The bagasse in the medium comprised the sole source of organic carbon for support of fungal growth. One inoculum "loop," a standard tool used in the preparation and culturing of microbes, was used to inoculate the medium.

*Pseudomonas putida*, a soil bacteria with wide catabolic capabilities, was maintained on nutrient agar. Minimal Inhibitory Concentration studies employed a mineral salts medium supplemented with 1% dextrose and 0.1% yeast extract. One inoculum "loop," a standard tool used in the preparation and culturing of microbes, was used to inoculate a plant sample.

(ii) In Situ Soil Materials

Fertile sandy loam topsoil in a cultivated field that had been used for the sequential cultivation of corn for the prior two years constituted the in situ environment. The field was located in the town Ingleside on the Eastern Shore of Maryland. The tissue burial and recovery work was completed in multiple marked plots.

(iii) Chemicals

The chemicals used in the following examples are:

Cinnamic Acid (Sigma-Aldrich Corporation, St. Louis, Mo., U.S.A) 2,6-Difluorocinnamic Acid (Sigma-Aldrich Corporation, St. Louis, Mo., U.S.A) alpha-Fluorocinnamic Acid (Sigma-Aldrich Corporation, St. Louis, Mo., U.S.A) 3-Cholorcinnamic acid (Sigma-Aldrich Corporation, St. Louis, Mo., U.S.A) 2-Chloro-4-hydroxybenzaldehyde (Sigma-Aldrich Corporation, St. Louis, Mo., U.S.A) 3,5-Dibromo-4-hydroxybenzaldehyde (Sigma-Aldrich Corporation, St. Louis, Mo., U.S.A)

EXAMPLE 3

Staining Methodologies

Techniques are described herein for treating thin, hand cut plant sections to estimate the amounts of plant polymer materials, such as lignin, and of fungal cell wall materials, such as chitin, in and around those plant sections.

Staining intensity ratings were subjectively established on ten-point rating scales and used as qualitative rankings within each individual example. Unless otherwise indicated, staining for lignin present in bagasse was performed by both the phlorgluciol and hypochlorite/sulfite techniques and was rated subjectively on a ten-step scale, from most intense staining (9) to no staining (0). Staining for chitin present in the bagasse was also subjectively rated on a ten-step scale from most intense staining (9) to no staining (0). All staining techniques were performed in triplicate, unless otherwise indicated. Thus, a high lignin stain and low chitin stain recovered from a treeated plant sample indicates that there are few microorganisms in or on the plant sample and that lignin has not degraded by any extensive amount.

These valuations should be considered as qualitative comparisons or rankings and not as quantitative determinations both within individual examples and between different examples.

(i) Lignin

Technique 1: Place sections in a drop of saturated, aqueous phloroglucinol in 20% HCl. Lignin appears as deep red (9) to light purple (1).

Technique 2: Place sections in commercial hypochlorite bleach for five minutes and transfer to a 1% solution of sodium sulfite. Lignin appears as a bright red cherry color (9) that fades to brown (1) in approximately 1 hour.

(ii) Chitin (Fungal Hyphae)

Technique: Sections are autoclaved in saturated KOH for 10 minutes to convert chitin to chitosan. Washed sections are placed in a few drops of iodine-potassium iodide solution (2 gm KI in 100 ml water and add 0.2 gm I2) in 1% sulfuric acid. Abundant amounts of chitosans appear dark violet (9) and a lower concentration as a light blue stain (1). Care should be exercised since cellulose may also stain under these conditions. For this reason, if necessary, cellulose can be removed by flooding with Schweitzer's reagent (saturated copper hydroxide in ammonium hydroxide) prior to iodine-potassium iodide treatment.

EXAMPLE 4

The Effects Halogen-Substituted Cinnamic Acid and Benzaldehyde Upon Lignin Staining Intensity in Sugarcane Five grams of a halogen-substituted, modified precursor molecule, such as 2,6-difluorocinnamic acid, 3-cholorcinnamic acid, or 2-Chloro-4-hydroxybenzaldehyde, were applied, by drench, to the roots of sugar cane plants at four weeks and also at two weeks before harvesting. Similarly, five grams of a chemically unmodified cinnamic acid was applied by drench to a plant sample at four weeks and at two weeks before harvesting, to serve as a control.

Lignin staining, according to any one of the methods described in Example 3 (i), was then performed on extracted bagasse and the intensity of the staining recorded. Bagasse was extracted according to the methodology described in Example 1 above.

Table 1 shows that none of the modified precursors affects the intensity of staining. Since the intensity of lignin staining is indicative of the amount of lignin present in any given sample, the fact that the sugar cane samples did not differ in staining intensity from the control samples ("untreated control" and "cinnamic acid") indicates that none of the modified precursors affects the quantity of lignin amassed in the sugar cane plant sample.

For instance, neither the addition of the normal, unmodified lignin precursor, cinnamic acid, nor the addition of halogenated, 2,6-difluorocinnamic acid resulted in increased staining.

Thus, this control study establishes that the modified precursors of the present invention do not, themselves, adversely, or otherwise, affect the quantity, abundance or accumulation of lignin in sugar cane plants.

TABLE 1

| Treatment/Agent Number | Lignin stain intensity |
| --- | --- |
| Untreated Control | 8 |
| Cinnamic Acid | 8 |
| 2,6-Difluorocinnamic Acid | 8 |
| alpha-Fluorocinnamic Acid | 8 |
| 3-Cholorcinnamic Acid | 8 |
| 2-Chloro-4-hydroxybenzaldehyde | 8 |
| 3,5-Dibromo-4-hydroxybenzaldehyde | 8 |

EXAMPLE 5

Halogen-Substituted Cinnamic Acid and Benzaldehyde and Their Effects Upon the Growth of White-Rot Fungus In similar fashion to Example 4, sugar cane plants were treated at four weeks and also at two weeks before harvest, with five grams of the modified precursors described above, by drenching the sugar cane roots. Bagasse samples were then obtained and approximately 10 g used in the following experiment.

In this experiment, white-rot fungus was cultured on the bagasse samples for three months. Specifically, *P. chrysosporium* was maintained on PDA and then added to a liquid mineral salt medium that contained the treated plant materials, such as treated bagasse. One inoculum "loop," a standard tool used in the preparation and culturing of microbes, was used to inoculate the bagasse-containing medium. The medium with the bagasse comprised the only sole source of organic carbon for support of fungal growth. After culturing the fungus on the bagasse stored in the liquid medium, the bagasse was collected from the medium and then stained for lignin and chitin.

Figure 3:
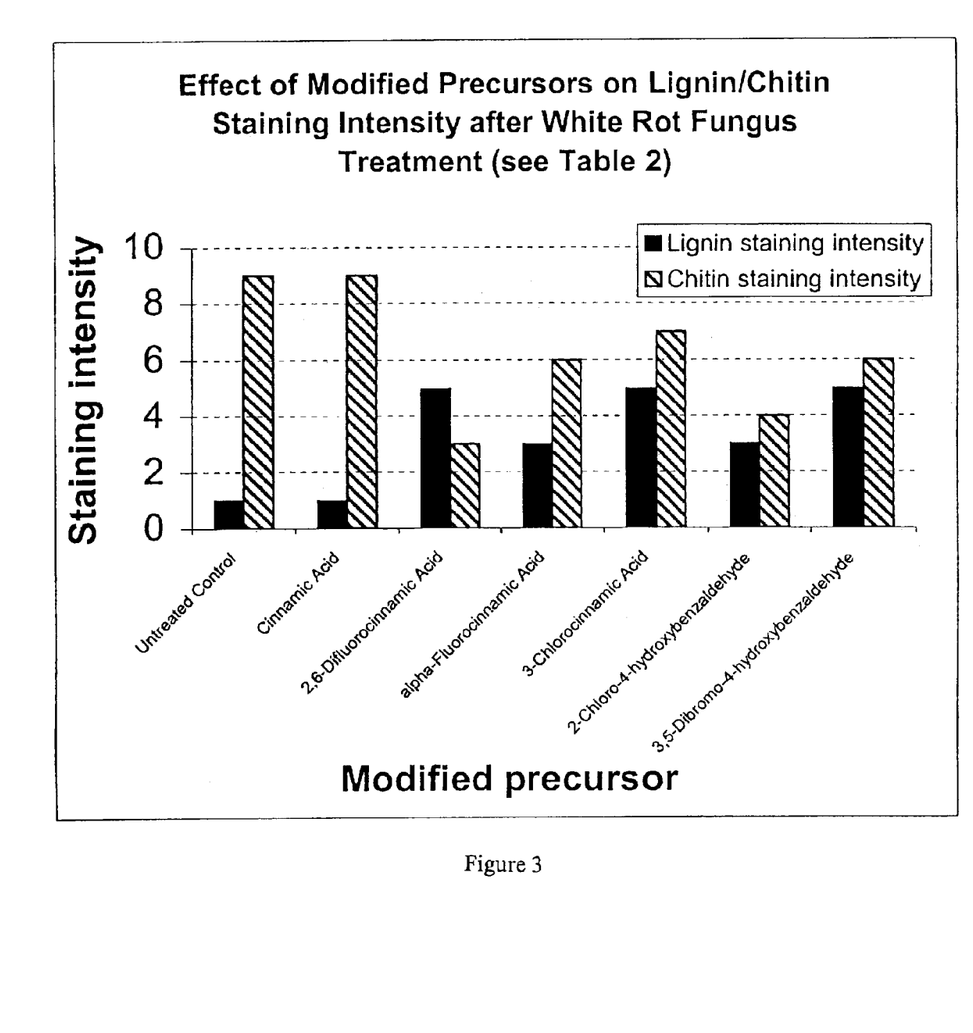
FIG. 3 shows the effect of treating sugar cane with different modified precursors with respect to the ability of white-rot fungus to degrade bagasse extracted from the treated sugar cane, as measured by relative lignin and chitin staining intensities. See Example 5 and Table 2.

As can be seen from Table 2, and as represented graphically in FIG. 3, the staining intensity of chitin was less intense when the sugar cane plant was treated with a modified precursor molecule, than the controls. Accordingly, this means that the growth of white-rot fungus, and thus, the accumulation of chitin, was inhibited in bagasse samples treated with a halogenated precursor molecule.

These findings correlate with the concept that fungal activity decomposes lignin. The inventor found that lignin staining intensity was low when chitin, that is, when the fungal population, was high in the control samples. Conversely, more lignin was available for staining in those samples that were treated with a modified precursor.

TABLE 2

| Treatment/Agent Number | STAINING INTENSITY | |
| --- | --- | --- |
| | Lignin | Chitin |
| Untreated Control | 1 | 9 |
| Cinnamic Acid | 1 | 9 |
| 2,6-Difluorocinnamic Acid | 5 | 3 |
| alpha-Fluorocinnamic Acid | 3 or 4 | 6 |
| 3-Chlorocinnamic Acid | 5 | 7 |
| 2-Chloro-4-hydroxybenzaldehyde | 3 | 4 |
| 3,5-Dibromo-4-hydroxybenzaldehyde | 5 | 6 |

EXAMPLE 6

Dosage-Dependent Effects of Cinnamic Acid and Halogen-Substituted Cinnamic Acid on the Growth of White-Rot Fungus Sugar cane plants were treated with either 0.5 g, 5 g or 50 g of 2,6-difluorocinnamic acid or 3-cholorcinnamic acid four weeks prior to harvest and also at two weeks prior to harvest. Thus, the total dosage of each modified precursor is either 1 g, 10 g, or 100 g. White-rot fungus was then cultured on the extracted bagasse samples for three months and lignin and chitin staining performed.

Figure 4:
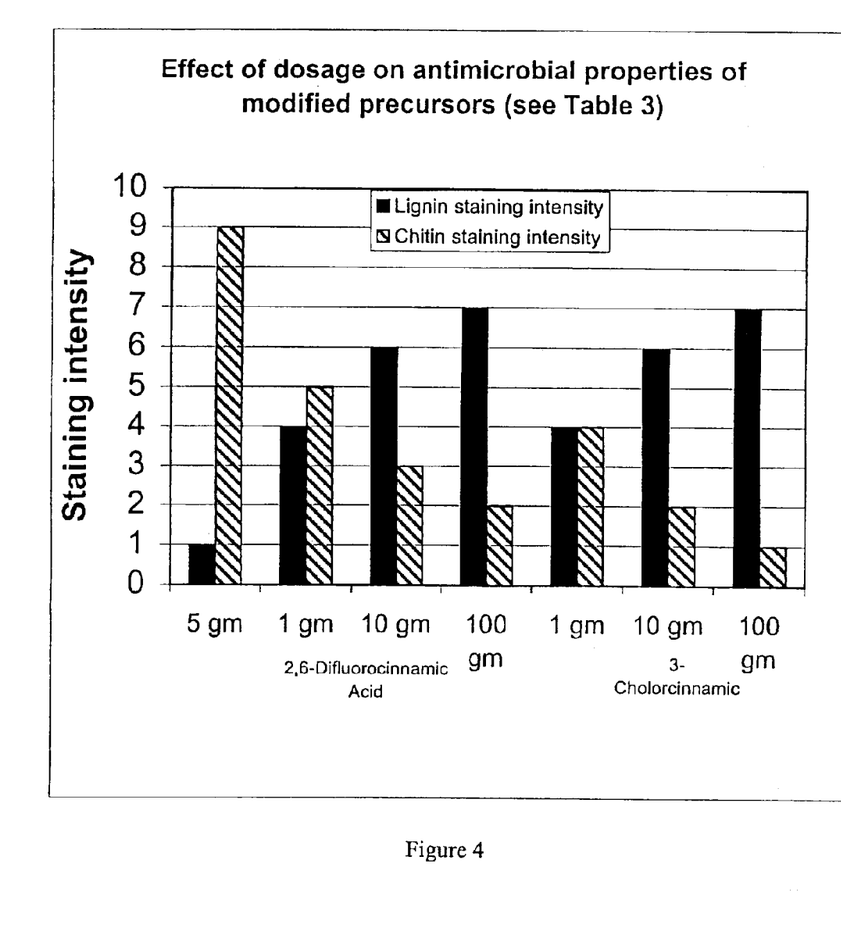
FIG. 4 shows the effect of treating sugar cane with different doses of either 2,6-difluorocinnamic acid or 3-chlorocinnamic acid modified precursors upon the ability of white-rot fungus to degrade bagasse extracted from the treated sugar cane. See Example 6 and Table 3.

There is a broad dose response evident that relates the amount of applied modified precursor and the decrease in fungal biomass. See Table 3 and FIG. 4. This relationship is consistent with an antimicrobial mechanism of activity.

TABLE 3

| Treatment/Agent Number | STAINING INTENSITY | |
| --- | --- | --- |
| | Lignin | Chitin |
| Untreated Control | 1 | 9 |
| 2,6-Difluorocinnamic Acid | | |
| 1 gm | 4 | 5 |
| 10 gm | 6 | 3 |
| 100 gm | 7 | 2 |
| 3-Cholorcinnamic Acid | | |
| 1 gm | 4 | 4 |
| 10 gm | 6 | 2 |
| 100 gm | 7 | 1 |

The rate and extent of lignin degradation by white-rot fungus is a function of the amount of halogen-substituted cinnamic acid incorporated into the lignin. That rate and extent can be controlled by the specific halogen-substituted cinnamic acid applied as well as the dose and timing of the applications.

EXAMPLE 7

Demonstration of the Presence and Potency of Antimicrobial Compounds During Sugarcane Bagasse Lignin Degradation Twenty milliliters of liquid medium was collected from cultures that were duplicate to those described in Example 6. Equivalent weights of bagasse had initially been added to each culture and the cultures were maintained for three months. Substantially greater amounts of the bagasse materials had been degraded in the untreated control culture. However, weight measurements were not taken due to the unknown contributions of fungal biomass. That liquid medium was filtered through a 0.2-micron filter and reduced to dryness by lyophilization. This dry material was weighed, suspended in sterile phosphate buffered saline and the MIC of this material was determined using standard microbial techniques that measure the amount of material required to establish a zone of inhibition by a pre-loaded antimicrobial material containing disc. The test microorganism used to determine MIC values was the common soil bacterium, *P. putida*. The MIC values are expressed on a per milliliter equivalent basis which better compares the relative potency and the quantity of these antimicrobial materials produced during biodegradation. This method is herein referred to as an "MIC screening assay."

The potency of the antimicrobial compounds released into and present in the culture media via the action of white-rot fungal degradation is much increased in halogen-substituted cinnamic acid treated bagasse materials. That increased potency, expressed as a lower MIC value (on a per milliliter basis), is greater after treatment of plants with higher levels of the modified precursors. The MIC value for the untreated control was not clearly established due to lack of sufficient material and potency.

Table 4 Halogen-substituted lignin materials release more potent antimicrobial molecules than do the degradation products of control lignin samples.

| Treatment/Agent Number | MIC |
| --- | --- |
| Untreated Control | >10 |
| 2,6-Difluorocinnamic Acid | |
| 1 gm | 5 |
| 10 gm | 5 |
| 100 gm | 2.5 |
| 3-Cholorcinnamic Acid | |
| 1 gm | 5 |
| 10 gm | 2.5 |
| 100 gm | 1.25 |

EXAMPLE 8

Effects of Glyphosine Treatment and Halogen-Substituted Cinnamic Acid and Benzaldehyde on the Growth of White-Rot Fungus Glyphosine (Sigma Aldrich) is commercially available as a sugarcane ripener for use several weeks before harvest. In this example, glyphosine, at one-fourth the label rate (i.e., approximately 4 oz per acre), was added to 3-chlorocinnamic acid during drench treatments of 5 gm, both four weeks and two weeks prior to harvest. The label rate of glyphosine was 16 oz. White-rot fungus was cultured on the bagasse samples for three months according to the methodology described in Example 2.

TABLE 5

| | STAINING INTENSITY | |
| --- | --- | --- |
| Treatment/Agent Number | Lignin | Chitin |
| Untreated Control | 1 | 8 |
| 3-Chlorocinnamic Acid | | |
| 10 gm. | 5 | 3 |
| 10 gm with Glyphosine | 7 | 2 |
| 2-Chloro-4-hydroxybenzaldehyde | | |
| 10 gm. | 6 | 3 |
| 10 gm with Glyphosine | 7 | 2 |

Glyphosine, when used at one fourth the label rate, that is when 4 oz of glyphosine is added to the modified precursor, increases the effectiveness of the recalcitrance of lignin to biodegradation by white-rot fungi that is conferred by halogen-substituted precursors. Thus, herbicides, herbicide safners and plant growth regulators may be used to enhance halogen-substituted precursor treatments for increasing carbon sequestration.

EXAMPLE 9

Effects of In Situ Degradation of Bagasse Obtained from Halogen-Substituted Cinnamic Acid and Benzaldehyde Treated Sugarcane Plants Sugar cane plants were treated four weeks and two weeks before harvest with drench applications of 10 grams of one of the chemicals listed in Table 6, i.e., cinnamic acid, 2,6-difluorocinnamic acid, 3-chlorocinnamic acid or 2-chloro-4-hydroxybenzaldehyde. Approximately, 10 g of extracted bagasse samples were mixed equally with sand, and the mixture placed into a nylon sack and buried approximately 6 inches below the ground. The samples were buried in such a fashion for six months from the March through August time period. All staining was done in quintuplicate.

Lignin biodegradation was shown to be slowed down in bagasse samples extracted from sugar cane plants that had been treated with halogen-substituted cinnamic acids and benzaldehyde. These results mirror results obtained from the in vitro lignin staining and chitin staining. Thus, the process of applying a modified precursor treatment to a plant to retard lignin degradation works just as well in the soil as in laboratory conditions. That is, the bagasse extract of sugar cane plants treated with a modified precursor worked to slow down degradation of lignin in soil organic matter.

TABLE 6

| | STAINING INTENSITY | |
| --- | --- | --- |
| Treatment/Agent Number | Lignin | Chitin |
| Untreated Control | 1 | 7 |
| Cinnamic Acid | 1 | 8 |
| 2,6-Difluorocinnamic Acid | 5 | 4 |
| 3-Cholorcinnamic Acid | 6 | 3 |
| 2-Chloro-4-hydroxybenzaldehyde | 6 | 3 |

EXAMPLE 10

Effects of In Situ Degradation of Corn Stalk Obtained from Cinnamic Acid, Halogen-Substituted Cinnamic Acid and Benzaldehyde-Treated Corn Plants Treatment of corn plants included two sprays, both one month after seedling emergence and once at tasseling with a spray application of 20 mM of one of the chemicals listed in Table 7, i.e., cinnamic acid, 2,6-difluorocinnamic acid, 3-chlorocinnamic acid or 2-chloro-4-hydroxybenzaldehyde with a silicone spreader/sticker until runoff. Dried stalk samples were buried in soil, as described above, for six months from the March through August time period. All staining was done in quintuplicate.

As demonstrated with the sugar cane-extracted bagasse samples, the degradation of lignin from corn plants treated with halogen-substituted precursor molecules was slowed down. That is, there was less lignin degradation as measured by lignin staining intensity, in treated corn plants than compared with the untreated and unmodified precursor treated control samples. The results from corn are essentially the same as those obtained from the in situ studies of sugar cane. Thus, a modified precursor of the present invention can be applied to a variety of plants and is not limited to use with sugar cane or corn.

TABLE 7

| Treatment/Agent Number | STAINING INTENSITY | |
|---|---|---|
| | Lignin | Chitin |
| Untreated Control | 1 | 8 |
| Cinnamic Acid | 0–1 | 9 |
| 2,6-Difluorocinnamic Acid | 5 | 6 |
| 3-Cholorcinnamic Acid | 7 | 4 |
| 2-Chloro-4-hydroxybenzaldehyde | 6 | 3 |

EXAMPLE 11

Effects of Glyphosate Combined with Cinnamic Acid and with Halogen-Substituted Cinnamic Acids Treated Stalk Materials of Corn in White-Rot Fungus Based Degradation Studies Glyphosate (Sigma Aldrich) is commercially available as a no-till herbicide for use with corn. In this example glyphosate at the one-fourth the label rate (i.e., approximately 3 oz per acre) was added to 3-chlorocinnamic acid. The label rate of glyphosate was 12 oz per acre. The glyphosate was applied through a spray treatment that included two sprays, both one month after seedling emergence and once at tasseling. The glyphosate was applied as a spray application that included 20 mM of one of the chemicals listed in Table 8. The spray application was applied with a silicone spreader/sticker until runoff. White-rot fungus was cultured on potato dextrose agar and then use to inoculate a medium containing the corn stalk fibrous extract as described in Example 2 above. These samples were cultured under appropriate conditions for three months.

The results indicate that glyphosate increases the effectiveness of halogen-substituted precursor molecules in reducing lignin biodegradation by white-rot fungi. Thus, inhibitors of aromatic biosynthesis can be used to enhance the effectiveness of a modified precursor in slowing down the rate of lignin degradation and, in so doing, help increase carbon sequestration by soil organic material.

TABLE 8

| Treatment/Agent Number | STAINING INTENSITY | |
|---|---|---|
| | Lignin | Chitin |
| Untreated Control | 2 | 8 |
| 3-Chlorocinnamic Acid | 6 | 3 |
| with Glyphosate | 7 | 2 |

EXAMPLE 12

Use of Fungicidal Candidates to Increase Plant Resistance to Degradation After Harvest Two year old seedlings of Tulip trees (*Liriodendron tulipifera*) and White pine (*Pinus strobus*) were cultivated in pots and fungicidal candidates were applied via an injection application to the base of the stem at approximately 100 ppm (parts per million) of fungicidal candidate, on a weight basis of the weight of the treated plant. Fungicidal candidates were mixed into an aqueous methanol solution at a concentration of 1 gram per liter and injected into stems under constant pressure via an injection employing a syringe and hypodermic needle. Examples of fungicidal candidates that were injected include thiabendazole (2-(4-thiazolyl) benzimidazole)), carbendazim (methyl-2-benzimidazole carbamate) and propiconazole (1-[[2-(2,4-dichlorophenyl)-4-propyl-1,3-dioxolan-2-yl] methyl]-1H-1,2,4-triazole). All chemicals were purchased from Chem Service, Inc., West Chester, Pa.

Stems were harvested after 4 weeks, washed to remove soluble materials and then dried. Then, thin sections of the stem were made and tested for anti-fungal activity based on the uptake of a fungicidal candidate into the stem. Alternatively, thin sections were stained for lignin and chitin and visually inspected according to the methodology described in Example 3 above.

In a similar experiment, corn plants (*Zea mays* L.: inbred line B 73) were cultivated in pots and were exposed to a foliar spray of a fungicidal candidate of approximately 100 ppm of fungicidal candidate, on a weight basis of the weight of the treated plant. Fungicidal candidates were delivered to the corn plants in an aqueous spray containing a solvent and emulsifier adjuvant at a concentration of 1 gram per liter. Treated plants were harvested, dried and cut into several centimeter-long sections.

Sections were taken from nodal and from internodal regions at the base of the stalk for anti-fungal tests. Thin sections were made, stained for lignin and chitin, and visually inspected according to the methodology described in Example 3 above.

(i) Exposing Plants to Fungicidal Chemicals Does Not Alter Plant Development or Lignin Staining The size and/or growth patterns of Tulip trees, White pine and corn plants treated once four weeks prior to harvesting were not affected by application of these fungicidal candidates. Similarly, none of the three fungicidal candidates were phytotoxic to any of these plants.

Furthermore, the fungicidal candidates do not appear to affect the intensity of lignin staining or, by extrapolation, the quantity of lignin present in the plant stem material. See Table 9.

TABLE 9

| | Lignin Stain |
|---|---|
| Treatment/Agent - Tulip tree | |
| Untreated Control | 9 |
| Thiabendazole - 100 ppm application rate | 9 |
| Carbendazim - 100 ppm application rate | 9 |
| Propiconazole - 100 ppm application rate | 9 |
| Treatment/Agent - White Pine tree | |
| Untreated Control | 9 |
| Thiabendazole - 100 ppm application rate | 9 |
| Carbendazim - 100 ppm application rate | 9 |
| Propiconazole - 100 ppm application rate | 9 |
| Treatment/Agent - Corn plant | |
| Untreated Control | 9 |
| Thiabendazole - 100 ppm application rate | 9 |
| Carbendazim - 100 ppm application rate | 9 |
| Propiconazole - 100 ppm application rate | 9 |

(ii) The Effect of Fungicidal Candidates on White Rot Fungus Growth on Treated Plants Tulip tree, White Pine and corn plants were treated with fungicidal candidates four weeks before harvest. White rot fungus (*Phanerochaete chrysosporium*) was then cultured on the plant samples for three months. Staining and quantification of lignin and chitin present in plant materials was performed as described above. Staining was done in triplicate and the results are shown in Table 10.

TABLE 10

| Treatment/Agent - | Intensity of Lignin/ Chitin Stain | |
|---|---|---|
| a. Tulip tree | | |
| Untreated Control | 3 | 6 |
| Thiabendazole - 100 ppm application rate | 9 | 1 |
| Carbendazim - 100 ppm application rate | 8 | 1 |
| Propiconazole - 100 ppm application rate | 7 | 2 |
| b. White Pine tree | | |
| Untreated Control | 2 | 7 |
| Thiabendazole - 100 ppm application rate | 8 | 2 |
| Carbendazim - 100 ppm application rate | 7 | 2 |
| Propiconazole - 100 ppm application rate | 8 | 1 |
| c. Corn plant | | |
| Untreated Control | 2 | 8 |
| Thiabendazole - 100 ppm application rate | 9 | 1 |
| Carbendazim - 100 ppm application rate | 8 | 2 |
| Propiconazole - 100 ppm application rate | 8 | 1 |

Fungal growth was assessed by measuring the intensity of chitin stain as an indicator of the amount fungal hyphae mass. The results of Table 10 show that fungal growth is slowed down on plants treated with any one of the three fungicidal candidates prior to harvest. Accordingly, treatment with the fungicidal candidates results in a modification of plant materials that exhibit an increased resistance to degradation by White rot fungus.

What is claimed is:

1. A method for increasing the amount of organic material in a plant that is resistant to degradation, comprising exposing at least a part of a plant to a preparation of a modified lignin precursor, wherein at least some of the preparation is taken up by the plant and wherein the modified lignin precursor is incorporated into a macromolecule of the plant.

2. A method according to claim 1, wherein the modified precursor is a monolignol containing an chemical group that does not naturally occur in the plant.

3. A method according to claim 2, wherein the monolignol is selected from the group consisting of courmaryl, coniferyl, and sinapyl or any one of their aldehyde or acid derivatives thereof.

4. A method according to claim 1, wherein the macromolecule is a lignin or a lignincellulose.

5. The method of claim 2, wherein the monolignol comprises an unnaturally-occurring chemical group selected from the group consisting of a halogen, an amide, an amino, a nitro- group, a hydroxymethyl, a hydroxy, a sulfur, and a methyl.

6. A method according to claim 1, wherein said modified precursor comprises at least one of a C6-C1, C6-C2 or a C6-C3 molecule that comprises an unnaturally-occurring chemical group selected from the group consisting of a halogen, an amide, an amino, a nitro-group, a hydroxymethyl, a hydroxy, a sulfur, and a methyl.

7. A method for making a lignin prodrug, comprising:

(a) administering a preparation of a modified precursor to at least a part of a plant; and (b) growing the plant;

wherein at least some of said preparation is taken up by the plant; and wherein the modified precursor is incorporated into a natural macromolecule of the plant.

8. A method according to claim 7, wherein preparation is administered to the part of a plant, by at least one of a spray, injection, external application, or a drench.

9. A method according to claim 7, wherein the plant is any lignin-producing plant or any lignin-containing plant.

10. A method according to claim 7, wherein said plant is at the established growing phase of its developmental stage.

11. A method for slowing down the rate of plant degradation, comprising administering a modified lignin precursor comprising an unnaturally-occurring chemical group to a plant, wherein the modified lignin precursor is incorporated into the plant and confers increased resistance to biodegradation upon the plant, thereby slowing down the rate of plant degradation and increasing the ability of terrestrial soil to store carbon.

12. A method according to claim 11, wherein the unnaturally-occurring chemical group is selected from the group consisting of a halogen, an amide, an amino, a nitro-group, a hydroxymethyl, a hydroxy, a sulfur, and a methyl.

13. A method according to claim 11, wherein said lignin precursor is a monolignol containing an unnaturally-occurring chemical group selected from the group consisting of a halogen, an amide, an amino, a nitro- group, a hydroxymethyl, and a methyl.

* * * * *